US009763612B2

(12) United States Patent
    Siao (10) Patent No.: US 9,763,612 B2
(45) Date of Patent: Sep. 19, 2017

(54) LANCET REMOVAL MECHANISM FOR BLOOD SAMPLING DEVICE

(71) Applicant: MEDIFUN CORPORATION, Taichung (TW)

(72) Inventor: Shao-Lun Siao, Taichung (TW)

(73) Assignee: MEDIFUN CORPORATION, Taichung (TW)

( * ) Notice: Subject to any disclaimer, the term of this patent is extended or adjusted under 35 U.S.C. 154(b) by 356 days.

(21) Appl. No.: 14/623,450

(22) Filed: Mar. 5, 2015

(65) Prior Publication Data
    US 2015/0272616 A1    Oct. 1, 2015

(30) Foreign Application Priority Data
    Mar. 27, 2014    (TW) .............................. 103205313 U (51) Int. Cl.
    *A61B 17/14*    (2006.01)
    *A61B 5/151*    (2006.01)
    (Continued)

(52) U.S. Cl.
    CPC .......... *A61B 5/1519* (2013.01); *A61B 5/1513* (2013.01); *A61B 5/150022* (2013.01);
    (Continued)

(58) Field of Classification Search
    CPC ................ A61B 5/15; A61B 5/150007; A61B 5/150015; A61B 5/150022; A61B 5/15003; A61B 5/150038; A61B 5/150045; A61B 5/150106; A61B 5/150114; A61B 5/15016; A61B 5/150167; A61B 5/150175; A61B 5/150183; A61B 5/15019; A61B 5/150198; A61B 5/150374; A61B 5/150381; A61B 5/150389; A61B 5/150396; A61B 5/150404; A61B 5/150412; A61B 5/150419; A61B 5/150427; A61B 5/150435; A61B 5/150503; A61B 5/150511; A61B 5/150519; A61B 5/15186; A61B 5/1519; A61B 5/15188; A61B 5/15192; A61B 5/15194; A61B 5/15196; A61B 5/15198
    See application file for complete search history.

(56) References Cited

U.S. PATENT DOCUMENTS

6,045,567 A *   4/2000  Taylor .............. A61B 5/150022
                                                    600/573
6,197,040 B1 *  3/2001  LeVaughn ........ A61B 5/150022
                                                    600/583
(Continued)

*Primary Examiner* — Jonathan Miles (57) ABSTRACT

A lancet removal mechanism for a blood sampling device contains: a stop assembly, a trigger unit, and a control button. The stop assembly includes an inner protrusion. The trigger unit includes a lancet holder and a triggering shaft, wherein the lancet holder is fixed in the stop assembly and has an outer protrusion formed on an outer wall thereof to engage with the inner protrusion of the stop assembly, the lancet holder has an orifice defined therein, and the orifice has a first inner shoulder arranged on a top end thereof, the triggering shaft extends into the orifice of the lancet holder and has a first outer shoulder for engaging with the first inner shoulder of the lancet holder. Furthermore, the control button is fitted on a top end of the triggering shaft.

6 Claims, 7 Drawing Sheets

(51) Int. Cl.
*A61B 17/34* (2006.01)
*A61B 5/15* (2006.01)

(52) U.S. Cl.
CPC ...... *A61B 5/15113* (2013.01); *A61B 5/15117* (2013.01); *A61B 5/15194* (2013.01); *A61B 5/150412* (2013.01); *A61B 5/150503* (2013.01); *A61B 17/34* (2013.01)

(56) References Cited

U.S. PATENT DOCUMENTS

| | | | | |
|---|---|---|---|---|
| 6,602,268 B2 * | 8/2003 | Kuhr | A61B | 5/15186 |
| | | | | 606/181 |
| 7,867,244 B2 * | 1/2011 | Lathrop | A61B | 5/150022 |
| | | | | 606/181 |
| 7,909,842 B2 * | 3/2011 | Flynn | A61B | 5/150022 |
| | | | | 606/181 |
| 7,914,547 B2 * | 3/2011 | Curry | A61B | 5/150022 |
| | | | | 606/181 |
| 7,955,348 B2 * | 6/2011 | Trissel | A61B | 5/150022 |
| | | | | 606/181 |
| 7,998,160 B2 * | 8/2011 | Lathrop | A61B | 5/150022 |
| | | | | 606/181 |
| 8,016,848 B2 * | 9/2011 | Lathrop | A61B | 5/150022 |
| | | | | 606/181 |
| 8,192,454 B2 * | 6/2012 | Flynn | A61B | 5/150022 |
| | | | | 606/181 |
| 8,246,645 B2 * | 8/2012 | Yoritaka | A61B | 5/150022 |
| | | | | 600/583 |
| 8,267,950 B2 * | 9/2012 | Robbins | A61B | 5/1411 |
| | | | | 606/182 |
| 8,388,639 B2 * | 3/2013 | Nicholls | A61B | 5/151 |
| | | | | 606/182 |
| 9,179,867 B2 * | 11/2015 | Schraga | A61B | 5/1411 |
| 9,271,667 B2 * | 3/2016 | Robbins | A61B | 5/1411 |
| 2009/0069832 A1 * | 3/2009 | Kitamura | A61B | 5/150022 |
| | | | | 606/181 |
| 2009/0228035 A1 * | 9/2009 | Kitamura | A61B | 5/150022 |
| | | | | 606/181 |
| 2009/0299398 A1 * | 12/2009 | Yoritaka | A61B | 5/150022 |
| | | | | 606/182 |

\* cited by examiner

LANCET REMOVAL MECHANISM FOR BLOOD SAMPLING DEVICE

FIELD OF THE INVENTION

The present invention relates to a blood sampling device, and more particularly to a lancet removal mechanism for the blood sampling device.

BACKGROUND OF THE INVENTION

A conventional blood sampling device is employed to sample patient's blood after inserting into skin, and its lancet is discarded after use.

As desiring to remove the lancet from a lancet holder, the lancet is rotated to remove from the lancet holder and then is inserted into a holding sleeve so as to be disposable with the holding sleeve, but the lancet pierces medical personnel easily.

The present invention has arisen to mitigate and/or obviate the afore-described disadvantages.

SUMMARY OF THE INVENTION

The primary objective of the present invention is to provide a lancet removal mechanism for a blood sampling device which prevents a lancet from being touched by medical personnel to enhance using safety and is operated easily with one hand.

To obtain the above objective, a lancet removal mechanism for a blood sampling device provided by the present invention contains: a stop assembly, a trigger unit, and a control button. The stop assembly includes an inner protrusion. The trigger unit includes a lancet holder and a triggering shaft, wherein the lancet holder is fixed in the stop assembly and has an outer protrusion formed on an outer wall thereof to engage with the inner protrusion of the stop assembly, the lancet holder has an orifice defined therein, and the orifice has a first inner shoulder arranged on a top end thereof, the triggering shaft extends into the orifice of the lancet holder and has a first outer shoulder for engaging with the first inner shoulder of the lancet holder. Furthermore, the control button is fitted on a top end of the triggering shaft.

Preferably, the stop assembly includes a connector and a rotating tube, the connector has a through hole defined therein to insert the lancet holder, the rotating tube has the inner protrusion and is rotatably fitted with the connector between a first position and a second position, such that when the rotating tube is located at the first position, the inner protrusion of the rotating tube engages with the outer protrusion of the lancet holder, and when the rotating tube is located at the second position, the inner protrusion of the rotating tube disengages from the outer protrusion of the lancet holder.

Preferably, the lancet holder further has a cutout defined on the outer protrusion, such that when the rotating tube is located at the first position, the inner protrusion of the rotating tube inserts into the cutout of the lancet holder to engage with the outer protrusion of the lancet holder, and when the rotating tube is located at the second position, the inner protrusion of the rotating tube moves away from the cutout of the lancet holder to separate from the outer protrusion of the lancet holder.

Preferably, a top end of the triggering shaft extends out of the orifice of the lancet holder, and the triggering shaft has a second outer shoulder, the control button includes has a second inner shoulder for engaging with the second outer shoulder of the triggering shaft.

Preferably, the control button includes a housing and a pushing member, and the housing has an aperture, the pushing member is fixed in the aperture of the housing and is fitted on the top end of the triggering shaft, wherein the pushing member has the second inner shoulder formed on an inner wall thereof.

Preferably, the aperture of the housing has two opposite locking portions arranged on an inner wall thereof, the pushing member also has a loop and two extensions, and the loop has a second inner shoulder formed on an inner wall thereof, wherein the two extensions extend outwardly from an outer wall of the loop, and each extension has a retaining portion for engaging with each locking portion of the housing.

Preferably, the trigger unit further includes a cap for fitting with the top end of the triggering shaft, and the control button further includes a resilient returning element fitted on the triggering shaft and abutting against the loop of the pushing member and the cap.

DETAILED DESCRIPTION OF THE PREFERRED EMBODIMENTS

Figure 1:
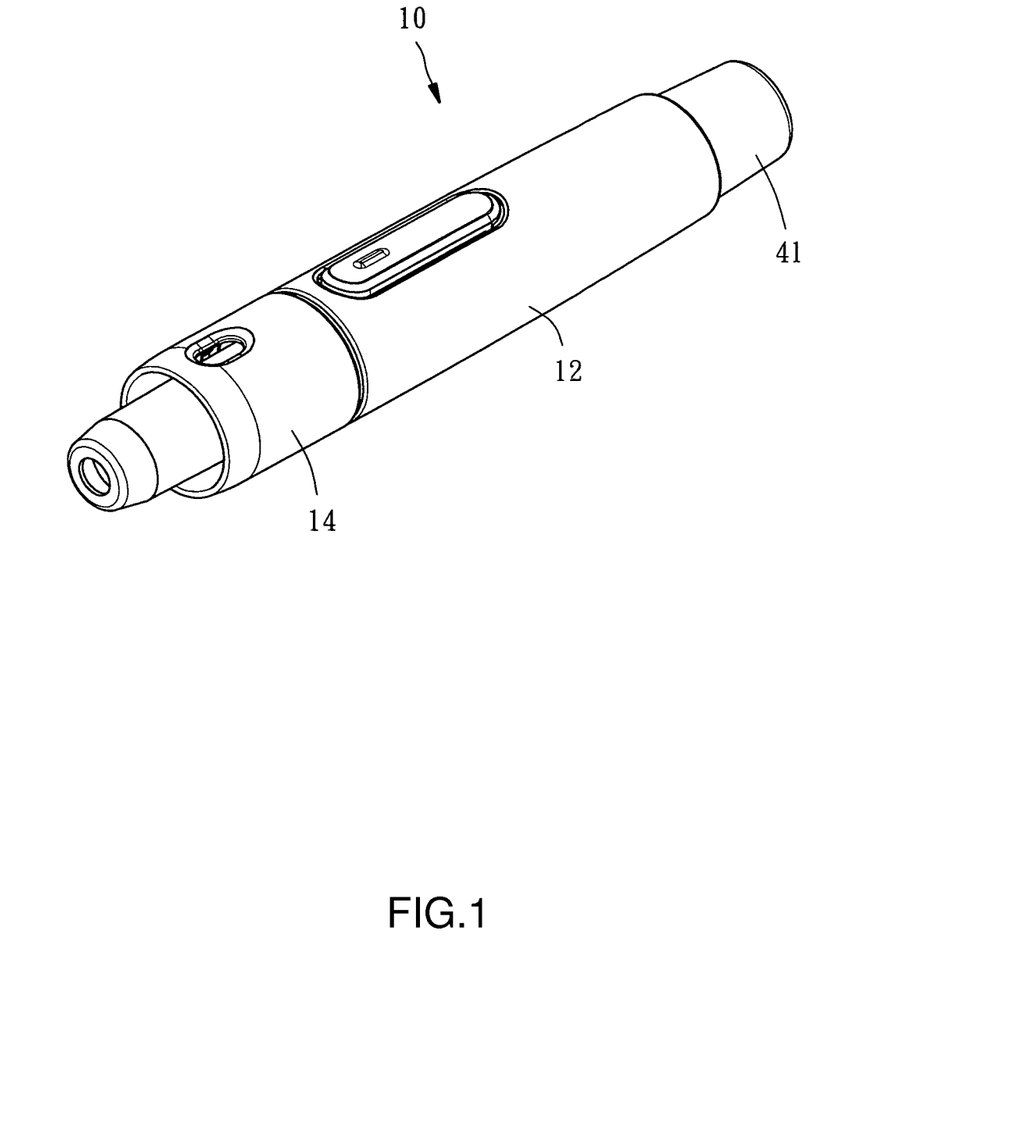
FIG. 1 is a perspective view showing the assembly of a blood sampling device according to a preferred embodiment of the present invention.
Figure 2:
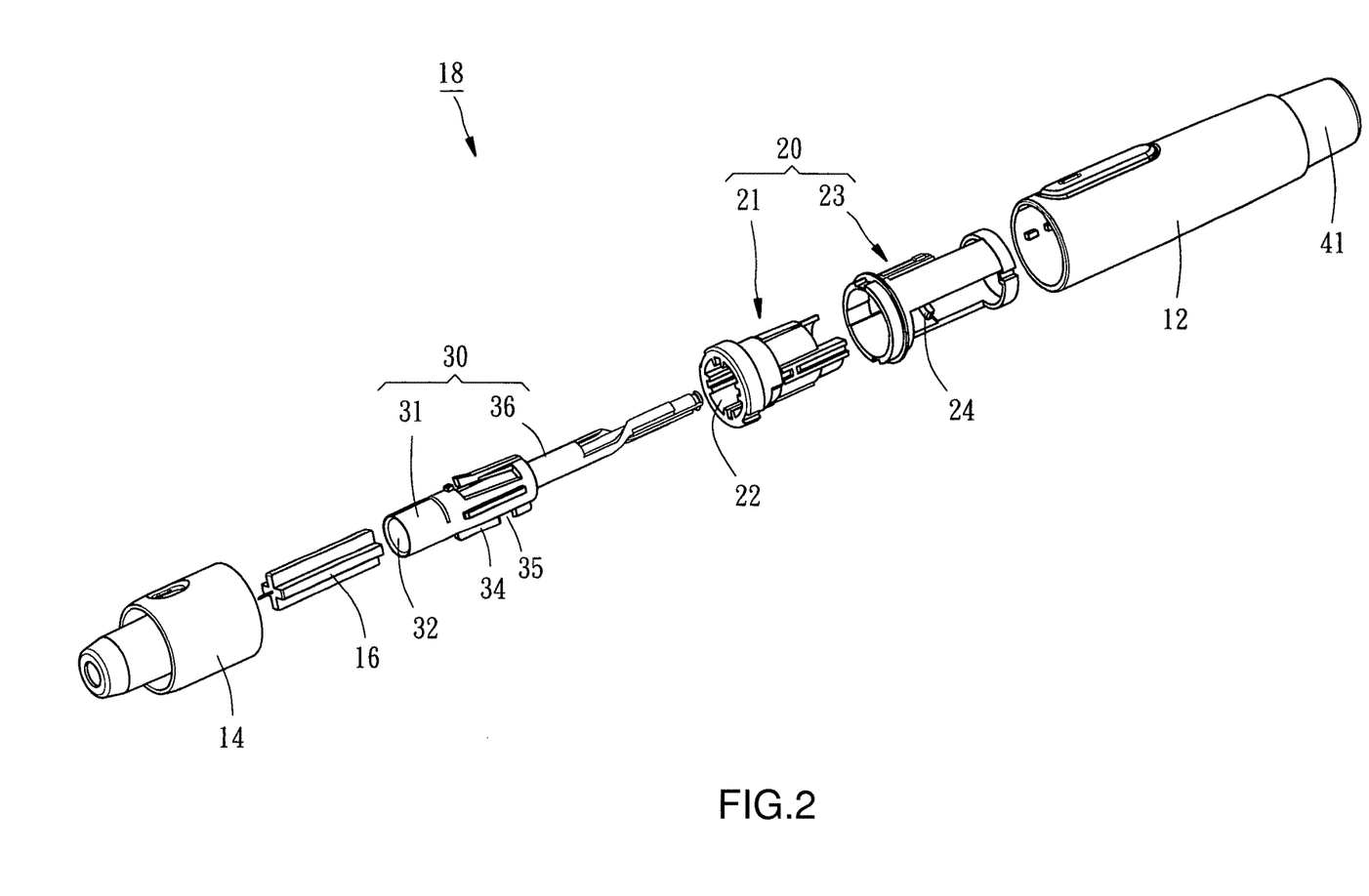
FIG. 2 is a perspective view showing the exploded components of a part of the blood sampling device according to the preferred embodiment of the present invention.

With reference to FIGS. 1 and 2, a blood sampling device 10 according to a preferred embodiment of the present invention comprises: a body 12 and a fitting tube 14 connected with a bottom end of the body 12. A lancet removal mechanism 18 is mounted in the blood sampling device 10 and includes a stop assembly 20, a trigger unit 30, and a control button 40.

The stop assembly 20 includes a connector 21 and a rotating tube 23, wherein the connector 21 is connected with a bottom end of the body 12 and is covered by the fitting tube 14, and the rotating tube 23 is rotatably fitted with the connector 21 and is fixed between the body 12 and the connector 21. In addition, the connector 21 has a through hole 22 defined therein, the rotating tube 23 has an inner protrusion 24 arranged on an inner wall thereof and located outside the through hole 22 of the connector 21.

Figure 5:
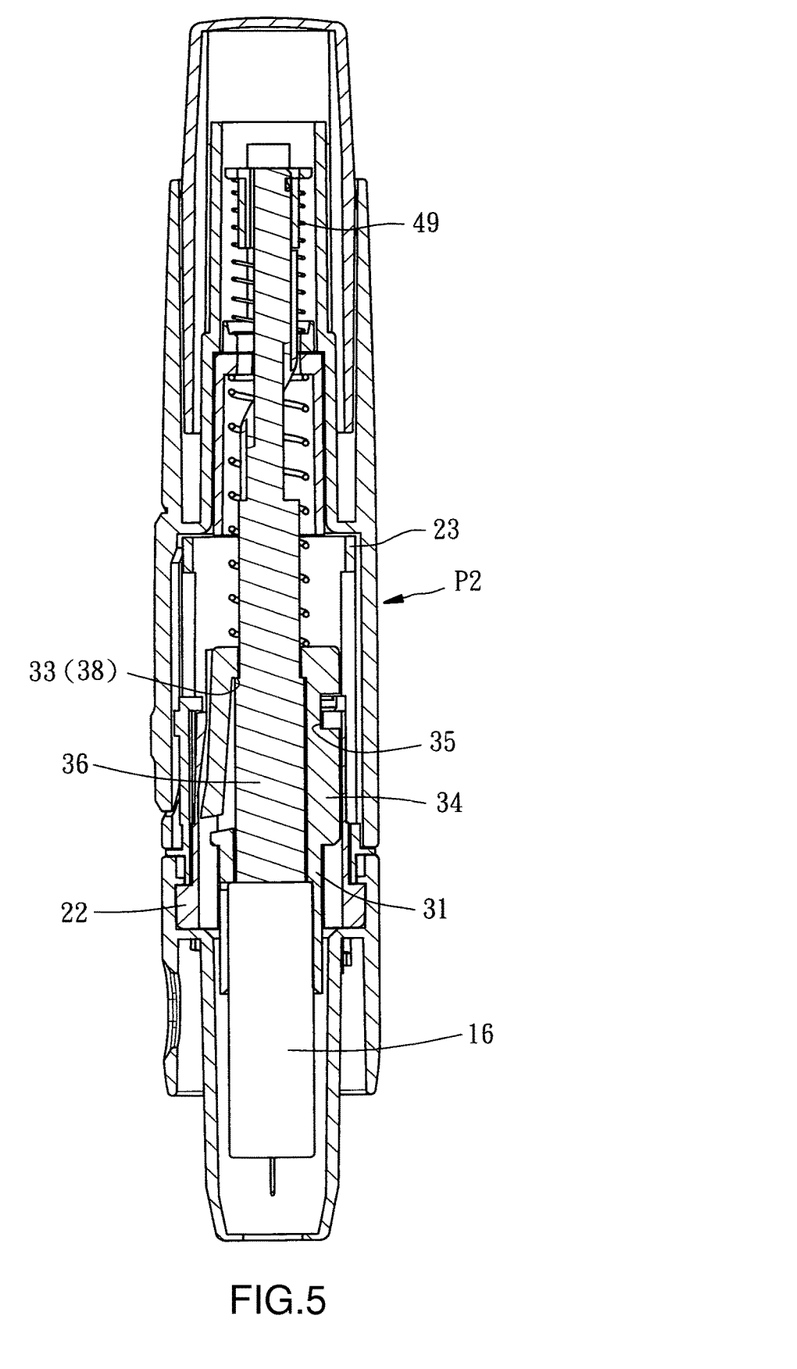
FIG. 5 is a cross sectional view showing the operation of the blood sampling device according to the preferred embodiment of the present invention.
Figure 6:
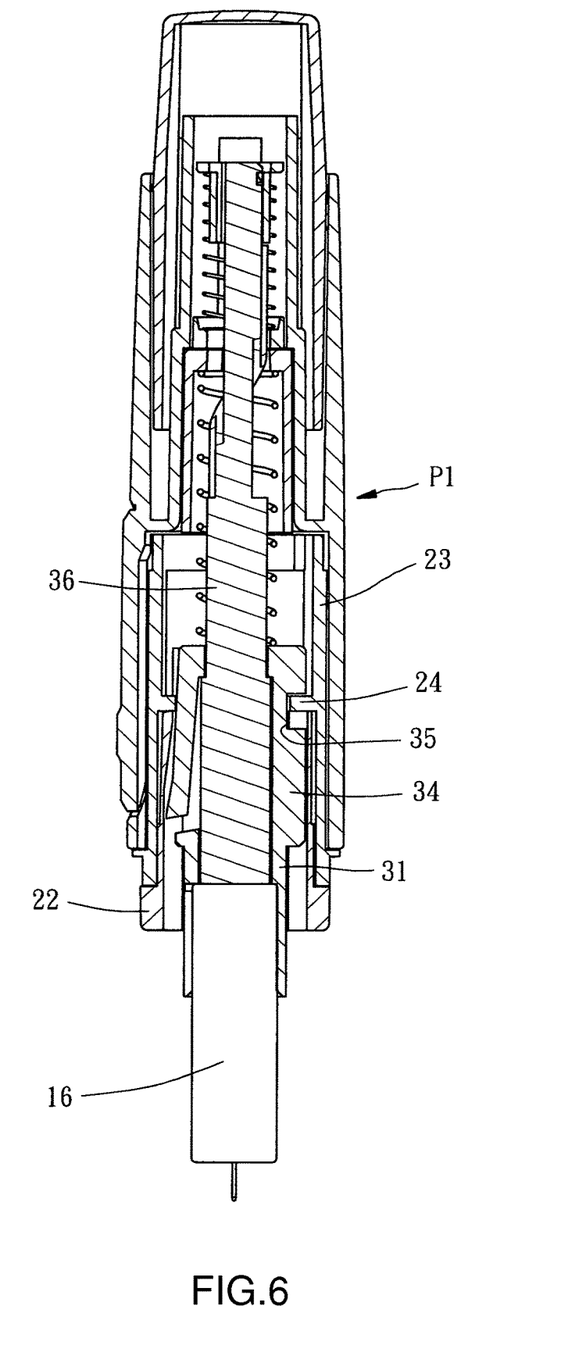
FIG. 6 is another cross sectional view showing the operation of the blood sampling device according to the preferred embodiment of the present invention.

The trigger unit 30 includes a lancet holder 31, as shown in FIG. 2, and the lancet holder 31 extends into the through hole 22 of the connector 21. The lancet holder 31 has an orifice 32 defined therein to fit with a lancet 16, and the orifice 32 has a first inner shoulder 33 arranged on a top end thereof (as shown in FIG. 5), the lancet holder 31 also has an outer protrusion 34 formed on an outer wall thereof and has a cutout 35 defined on the outer protrusion 34, such that when the rotating tube 23 is located at a first position P1, as illustrated in FIG. 6, the inner protrusion 24 of the rotating tube 23 inserts into the cutout 35 of the lancet holder 31 to engage with the outer protrusion 34 of the lancet holder 31, and the lancet holder 31 does not move in the through hole 22 of the connector 21. When the rotating tube 23 is located at a second position P2, as shown in FIGS. 5 and 6, the inner protrusion 24 of the rotating tube 23 moves away from the cutout 35 of the lancet holder 31 to separate from the outer protrusion 34 of the lancet holder 31, hence the lancet holder 31 moves upwardly and downwardly in the through hole 22 of the connector 21.

Figure 3:
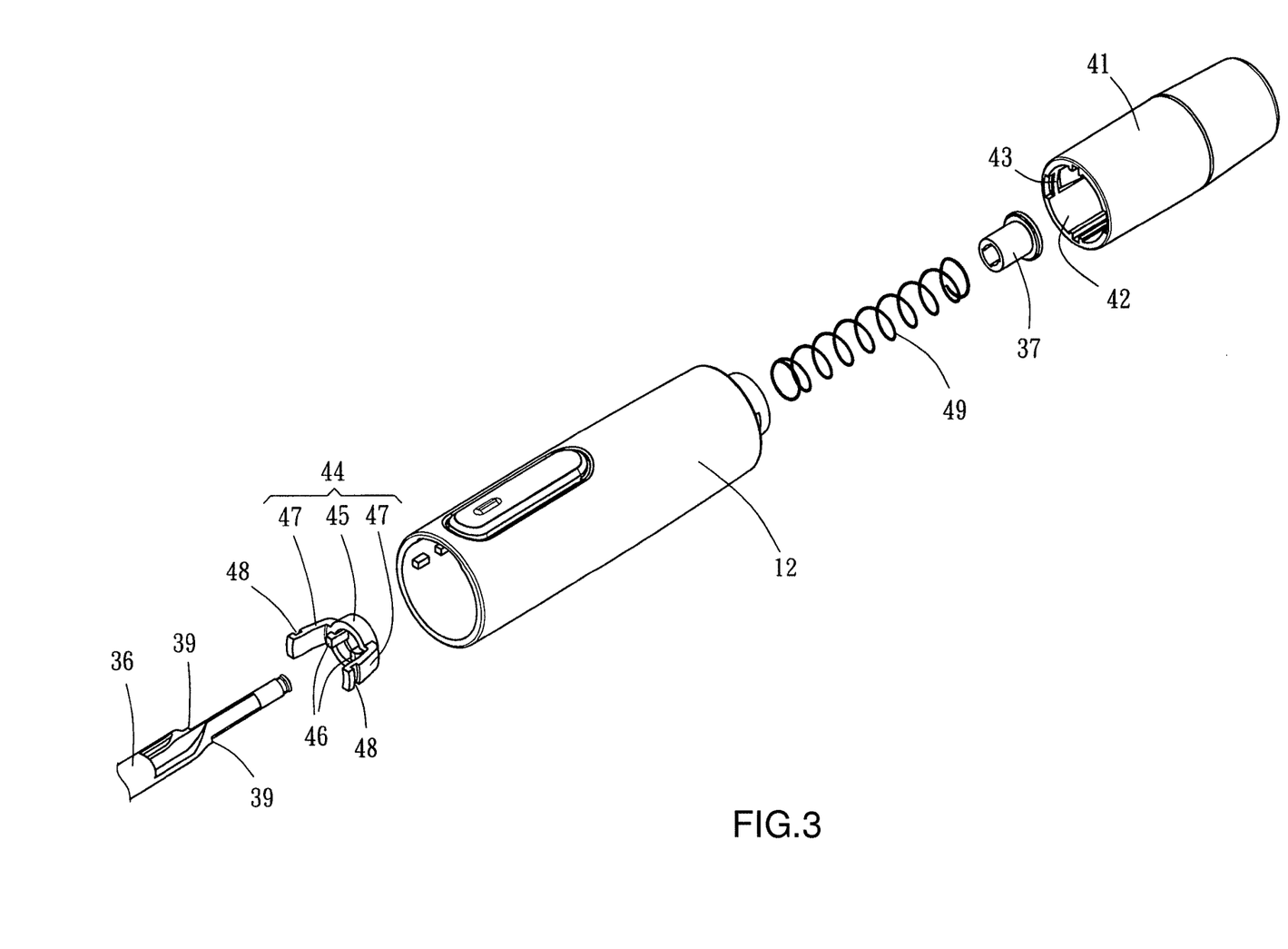
FIG. 3 is a perspective view showing the exploded components of another part of the blood sampling device according to the preferred embodiment of the present invention.

Referring further to FIGS. 2 and 3, the trigger unit 30 further includes a triggering shaft 36, wherein a bottom end of the triggering shaft 36 extends into the orifice 32 of the lancet holder 31 to trigger the lancet 16, and a top end of the triggering shaft 36 extends out of the orifice 32 of the lancet holder 31 to fit with a cap 37. The triggering shaft 36 has a first outer shoulder 38 defined on an outer wall thereof and has a second outer shoulder 39 above the first outer shoulder 38, wherein the first outer shoulder 38 engages with the first inner shoulder 33 of the lancet holder 31 (as shown in FIG. 5), such that the triggering shaft 36 drives the lancet holder 31 to move away from the lancet 16 in a loading process, and the triggering shaft 36 is driven by the lancet holder 31 to move toward the lancet 16 in a triggering process.

Figure 4:
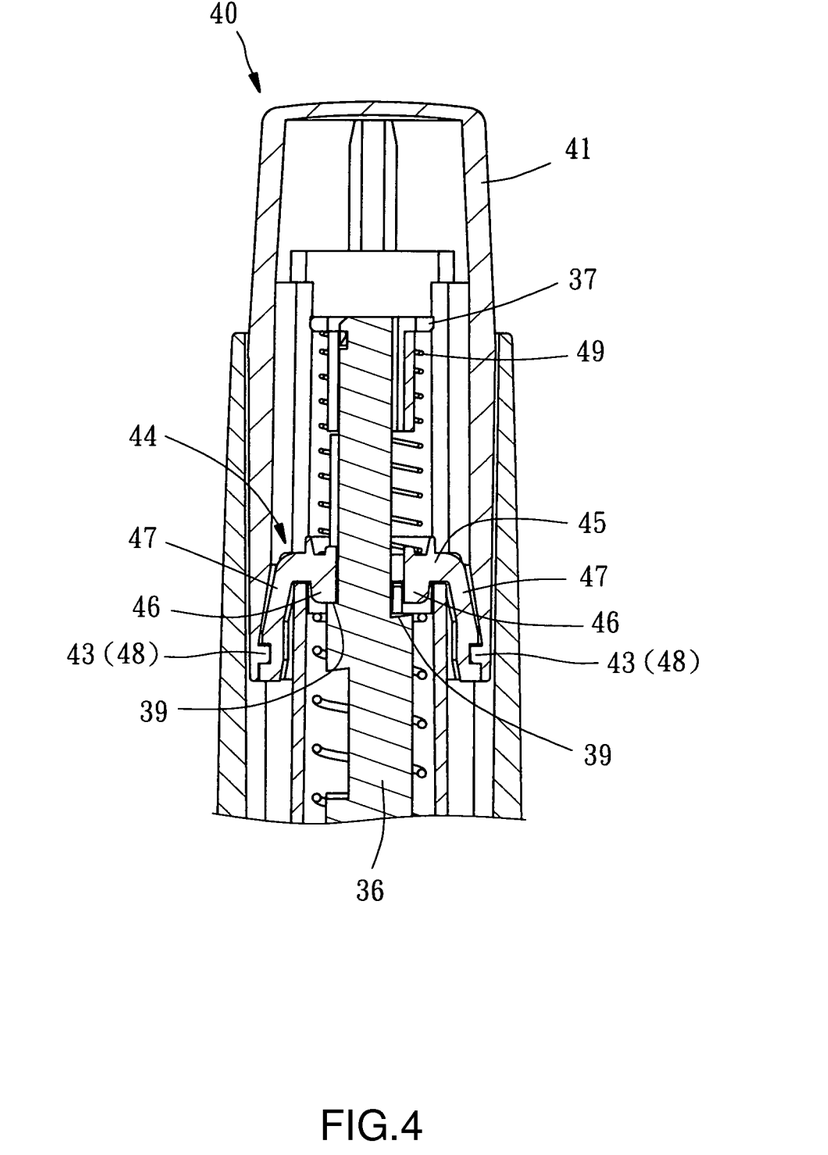
FIG. 4 is a cross sectional view showing the assembly of a part of the blood sampling device according to the preferred embodiment of the present invention.

With reference to FIGS. 3 and 4, the control button 40 includes a housing 41 and a pushing member 44. The housing 41 has an aperture 42 for fitting with a top end of the body 12, and the aperture 42 has two opposite locking portions 43 arranged on an inner wall thereof; the pushing member 44 has a loop 45 fitted on the top end of the triggering shaft 36, and the loop 45 has a second inner shoulder 46 formed on an inner wall thereof to engage with the second outer shoulder 39 of the triggering shaft 36. The pushing member 44 also has two extensions 47 extending outwardly from an outer wall of the loop 45, wherein each extension 47 has a retaining portion 48 for engaging with each locking portion 43 of the housing 41, such that the pushing member 44 is fixed in the aperture 42 of the housing 41. The control button 40 further includes a resilient returning element 49 fitted on the triggering shaft 36 and abutting against the loop 45 of the pushing member 44 and the cap 37 so as to push the triggering shaft 36 back to an original position.

Figure 7:
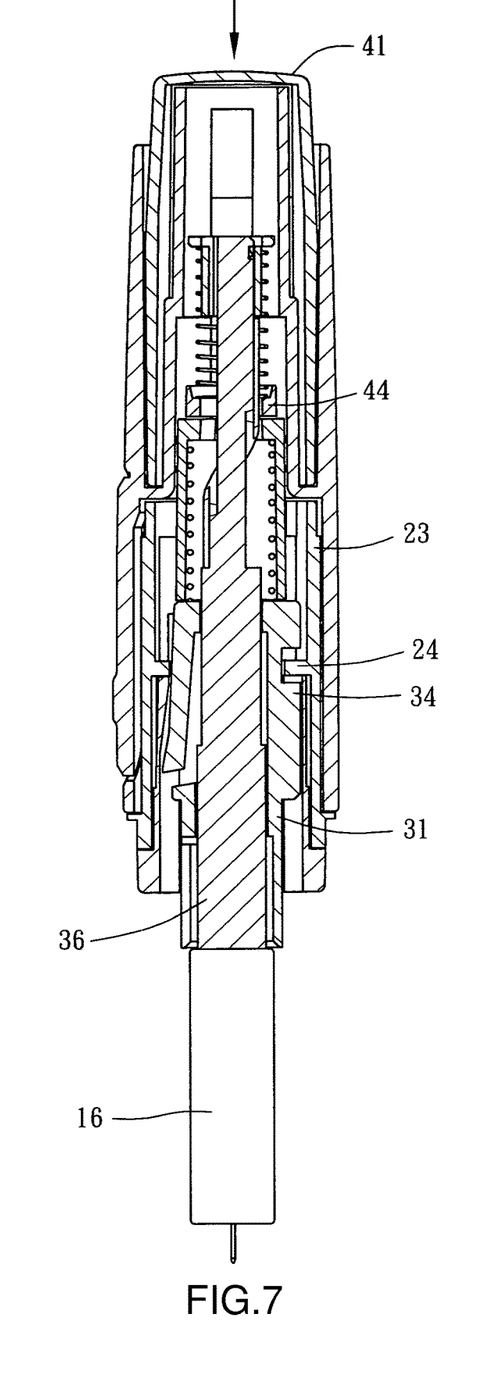
FIG. 7 is also another cross sectional view showing the operation of the blood sampling device according to the preferred embodiment of the present invention.

As desiring to remove the lancet 16, the fitting tube 14 is removed so that the lancet 16 exposes outside, and the rotating tube 23 is rotated toward the first position P1 (as shown in FIG. 6), then the lancet 16 is inserted on a holding sleeve (not shown), in the meantime, the lancet holder 31 does not move since it is limited by the rotating tube 23, then the control button 40 is pressed so that the pushing member 44 pushes the triggering shaft 36 downwardly, the lancet 16 is pushed out of the orifice 32 of the lancet holder 31, as illustrated in FIG. 7, and the control button 40 is released so that the triggering shaft 36 is pulled by the resilient returning element 49 to move back to the orifice 32 of the lancet holder 31, the lancet 16 is maintained on the holding sleeve and then is disposable with the holding sleeve. As desiring to sample blood by using the blood sampling device 10 again, the rotating tube 23 is rotated toward the second position P2 (as illustrated in FIG. 5) so that the lancet holder 31 moves upwardly and downwardly with the triggering shaft 36, thus replacing and installing a new lancet.

Thereby, the lancet removal mechanism prevents the lancet from being touched by medical personnel to enhance using safety and is operated easily with one hand.

While the preferred embodiments of the invention have been set forth for the purpose of disclosure, modifications of the disclosed embodiments of the invention and other embodiments thereof may occur to those skilled in the art. Accordingly, the appended claims are intended to cover all embodiments which do not depart from the spirit and scope of the invention.

What is claimed is:

1. A lancet removal mechanism for a blood sampling device comprising: a stop assembly including an inner protrusion; a trigger unit including a lancet holder and a triggering shaft, wherein the lancet holder is fixed in the stop assembly and has an outer protrusion formed on an outer wall thereof to engage with the inner protrusion of the stop assembly, the lancet holder has an orifice defined therein, and the orifice has a first inner shoulder arranged on a top end thereof, the triggering shaft extends into the orifice of the lancet holder and has a first outer shoulder for engaging with the first inner shoulder of the lancet holder; and a control button fitted on a top end of the triggering shaft, wherein the stop assembly includes a connector and a rotating tube, the connector has a through hole defined therein to insert the lancet holder, the rotating tube has the inner protrusion and is rotatably fitted with the connector between a first position and a second position, such that when the rotating tube is located at the first position, the inner protrusion of the rotating tube engages with the outer protrusion of the lancet holder, and when the rotating tube is located at the second position, the inner protrusion of the rotating tube disengages from the outer protrusion of the lancet holder.

2. The lancet removal mechanism for the blood sampling device as claimed in claim 1, wherein the lancet holder further has a cutout defined on the outer protrusion, such that when the rotating tube is located at the first position, the inner protrusion of the rotating tube inserts into the cutout of the lancet holder to engage with the outer protrusion of the lancet holder, and when the rotating tube is located at the second position, the inner protrusion of the rotating tube moves away from the cutout of the lancet holder to separate from the outer protrusion of the lancet holder.

3. The lancet removal mechanism for the blood sampling device as claimed in claim 1, wherein a top end of the triggering shaft extends out of the orifice of the lancet holder, and the triggering shaft has a second outer shoulder, the control button includes has a second inner shoulder for engaging with the second outer shoulder of the triggering shaft.

4. The lancet removal mechanism for the blood sampling device as claimed in claim 3, wherein the control button includes a housing and a pushing member, and the housing has an aperture, the pushing member is fixed in the aperture of the housing and is fitted on the top end of the triggering shaft, wherein the pushing member has the second inner shoulder formed on an inner wall thereof.

5. The lancet removal mechanism for the blood sampling device as claimed in claim 4, wherein the aperture of the housing has two opposite locking portions arranged on an inner wall thereof, the pushing member also has a loop and two extensions, and the loop has a second inner shoulder formed on an inner wall thereof, wherein the two extensions extend outwardly from an outer wall of the loop, and each extension has a retaining portion for engaging with each locking portion of the housing.

6. The lancet removal mechanism for the blood sampling device as claimed in claim 5, wherein the trigger unit further includes a cap for fitting with the top end of the triggering shaft, and the control button further includes a resilient returning element fitted on the triggering shaft and abutting against the loop of the pushing member and the cap.

* * * * *